(12) United States Patent
Rosenberg

(10) Patent No.: US 7,955,262 B2
(45) Date of Patent: Jun. 7, 2011

(54) METHOD AND APPARATUS FOR TREATMENT OF SKIN USING RF AND ULTRASOUND ENERGIES

(75) Inventor: Avner Rosenberg, Beit Shearim (IL)

(73) Assignee: Syneron Medical Ltd., Yokneam Illit (IL)

( * ) Notice: Subject to any disclaimer, the term of this patent is extended or adjusted under 35 U.S.C. 154(b) by 506 days.

(21) Appl. No.: 11/189,129

(22) Filed: Jul. 26, 2005

(65) Prior Publication Data
US 2007/0038156 A1 Feb. 15, 2007

(51) Int. Cl.
*A61B 8/00* (2006.01)
*A61B 18/18* (2006.01)
*A61F 2/00* (2006.01)
*A61H 1/00* (2006.01)

(52) U.S. Cl. .............. 600/439; 606/9; 607/101; 601/2; 600/437

(58) Field of Classification Search .............. 606/37–41, 606/27; 600/439; 601/2, 3; 607/99, 101
See application file for complete search history.

(56) References Cited

U.S. PATENT DOCUMENTS

| | | | |
|---|---|---|---|
| 5,405,368 A | 4/1995 | Eckhouse | |
| 5,786,924 A | 7/1998 | Black | |
| 5,871,524 A | 2/1999 | Knowlton | |
| 5,964,749 A | 10/1999 | Eckhouse et al. | |
| 6,234,990 B1 | 5/2001 | Rowe et al. | |
| 6,325,769 B1 | 12/2001 | Klopotek | |
| 6,425,912 B1 * | 7/2002 | Knowlton | 607/101 |
| 6,595,934 B1 | 7/2003 | Hissong | |
| 6,623,430 B1 * | 9/2003 | Slayton et al. | 600/439 |
| 6,662,054 B2 | 12/2003 | Kreindel et al. | |
| 6,702,808 B1 | 3/2004 | Kreindel | |
| 6,882,884 B1 | 4/2005 | Mosk et al. | |
| 6,889,090 B2 | 5/2005 | Kreindel | |
| 2003/0097162 A1 * | 5/2003 | Kreindel | 607/99 |
| 2004/0267252 A1 * | 12/2004 | Washington et al. | 606/27 |

(Continued)

FOREIGN PATENT DOCUMENTS

DE 299 06 921 9/1999

(Continued)

OTHER PUBLICATIONS

Francis A. Duck, "Electrical Property of Tissue," Academic Press Ltd., 1990, p. 200.

(Continued)

*Primary Examiner* — Unsu Jung
*Assistant Examiner* — Lawrence N Laryea
(74) *Attorney, Agent, or Firm* — The Nath Law Group; Susanne M. Hopkins; William L. Klima

(57) ABSTRACT

A system and method for treating skin. The System comprises one or more ultrasound transducers and one or more pairs of RF electrodes. The ultrasound transducers are adapted to focus ultrasound energy at one or more focal volumes in the skin. The RF electrodes are adapted to deliver RF energy to the one or more focal volumes. The method comprises heating the skin to a first temperature at one or more focal volumes in the skin by focusing ultrasound energy at the one or more focal volumes. The focal regions are then heated to a second temperature, the second temperature being higher than the first temperature, by generating an RF current in a region of the skin containing the focal regions.

37 Claims, 4 Drawing Sheets

U.S. PATENT DOCUMENTS

2005/0049582 A1 3/2005 DeBenedictis et al.
2006/0074355 A1* 4/2006 Slayton et al. .................... 601/2

FOREIGN PATENT DOCUMENTS

WO WO 02/094375 11/2002
WO WO 03/090366 10/2003

OTHER PUBLICATIONS

S. Gabriel, et al., "The dielectric properties of biological tissues: II. Measurements in the frequency range 10 Hz to 20 Hz," Phys. Med. Biol. 41 (1996) pp. 2251-2269.

* cited by examiner

METHOD AND APPARATUS FOR TREATMENT OF SKIN USING RF AND ULTRASOUND ENERGIES

FIELD OF THE INVENTION

The invention relates to non-invasive treatments of human tissue and more specifically to such treatments of skin.

BACKGROUND OF THE INVENTION

Skin rejuvenation is a medical aesthetic treatment, in which energy is applied to selected areas of the skin surface and/or to subcutaneous layers of the skin in order to achieve an improvement in the appearance of the treated skin. The most popular form of skin rejuvenation is the application of an amount of energy to the skin to heat target tissue to temperatures sufficiently above normal body temperature to induce desired effects in the tissue. The effects may be tissue damage, coagulation, ablation, destruction and necrosis. The specific effects achieved depend on the tissue, the temperature, and the period of time the tissue is maintained at the high temperature. This treatment improves the appearance of the skin by tightening the skin and reducing wrinkles, and by promoting regeneration in the skin layers and subcutaneous tissue.

Non-invasive delivery of energy to internal tissues has been done by directing electromagnetic energy or ultrasound energy to the skin surface. Electromagnetic radiation from a broad range of wavelengths has been used for heating the skin, including optical radiation, frequencies above 30 GHz, frequencies between 300 MHz to 30 GHz, and radio frequency (RF) energy. Typical RF frequencies used for skin treatment are between 100 kHz and 10 MHz. The technology, propagation through the body, interactions with the skin, and the effects on tissues are different for each part of the spectrum. Simultaneous application of optical energy and RF energy has also been used to treat skin.

U.S. Pat. No. 5,405,368 discloses the use of flash lamps for skin treatment. U.S. Pat. No. 5,964,749 describes a method and apparatus for treating skin which includes applying pulsed light to the skin to heat the skin in order to effect shrinking of collagen within the skin, thereby restoring the elasticity of the collagen and of the skin. The epidermis and outer layers of the skin may be protected by cooling with a transparent substance, such as ice or gel, applied to the skin surface. The temperature distribution within the skin is controlled by controlling the delay between the time the coolant is applied, and the time the light is applied, by controlling the pulse duration, applying multiple pulses, filtering the light and controlling the radiation spectrum. Preferably, the spectrum includes light having a wavelength in the range of 600-1200 nm. The pulsed light may be incoherent, such as that produced by a flashlamp, or coherent, such as that produced by a laser, and may be directed to the skin using a flexible or rigid light guide. U.S. Pat. Nos. 6,662,054 and 6,889,090 disclose the application of RF energy for subcutaneous treatment. U.S. Pat. No. 6,702,808 discloses a combination of light and RF energy for skin treatment. U.S. Pat. No. 5,871,524, describes application of radiant energy through the skin to an underlying subcutaneous layer or deeper soft tissue layers.

The main limitation on non-invasive skin treatment is the ability to transfer the energy through the outer layers of the skin and concentrating it to the required level in the target tissue, with minimal collateral damage to the surrounding tissue, including the tissue through which the energy must pass on its way to the target tissue. The solutions are based either on selective cooling or focusing of radiation. Focusing is possible when the wavelengths are sufficiently short, for example with optical radiation, millimeter and sub-millimeter waves, and high frequency ultrasound. Optical radiation is scattered inside the skin, so it is difficult to focus efficiently. Laser light is preferred in order to enable better focusing. U.S. Pat. No. 5,786,924 discloses a laser system for skin treatment. Published U.S. patent application Ser. No. 10/888356 to De Benedictis et al., having the publication number 2005/0049582, discloses using one or more light sources to generate microscopic treatment zones in skin in a predetermined pattern. The advantage of this approach is that the damaged tissue is localized to small volumes surrounded by healthy tissue, so that skin regeneration is faster.

High intensity focused ultrasound (HIFU) technology for non-invasive skin treatment is disclosed, for example, in U.S. Pat. Nos. 6,325,769 and 6,595,934. The last patent discloses the application of an array of focused ultrasound transducers, which generates an array of lesions in the skin or subcutaneous layers, with advantages similar to those disclosed in the above mentioned US Patent Application Publication 2005/0049582 but with minimal damage to the outer skin layer due to the focusing of the radiation. The resolution of the focusing of electromagnetic energy is limited by diffraction laws to about half of the wavelength. For less than a 0.5 mm focal dimension, a wavelength shorter than 1 mm is required. Although the application of electromagnetic energy at sub-millimeter wavelengths may have several advantages, generating sub-millimeter radiation is impractical for skin treatment due to its high cost. In RF applications, voltages and currents can be induced in body tissues by applying electrodes to the skin surface, which do not propagate as waves but rather fall into the quasi-static regime of the Maxwell equations. RF applications for non-invasive skin treatment are disclosed, for example, in U.S. Pat. Nos. 6,662,054, 6,889,090, 5,871,524. Typical RF frequencies used are between 100 kHz and 10 MHz. At these frequencies, the wavelength, which is between 3000 m and 30 m is much larger than any relevant dimension of the treated tissue. An AC current is induced in the skin by the applied AC voltage, generally obeying Ohm's law. RF technology is relatively simple and inexpensive, and very effective in transferring energy to a tissue. However it is difficult to localize it to a specific tissue layer. One method to generate selectivity is by cooling the skin surface, thereby creating a temperature gradient from the outside to the internal layers. Such a method is disclosed in U.S. Pat. No. 5,871,524.

SUMMARY OF THE INVENTION

The present invention provides a method and an apparatus for non-invasive treatment of skin and subcutaneous layers. In accordance with the invention, acoustic energy at ultrasound wavelengths is first directed to the skin surface. The ultrasound energy is focused onto one or more tissue volumes referred to herein as "focal volumes" in the skin or subcutaneous layer, below the skin surface. This provides a first heating of the tissue at the focal volumes of the ultrasound energy. RF energy is subsequently applied to the skin and the RF current is guided into the focal volumes preheated by the ultrasound energy. Without wishing to be bound by a particular theory, it is believed that this guiding effect is based on the temperature dependence of RF conductivity on temperature. In the temperature range of 20-90° C., and for RF frequencies between 100 kHz and 100 MHz, there is a positive slope of tissue electrical conductivity versus temperature (see for example, "Physical Properties of Tissue", by Francis A. Duck, Academic Press Ltd., 1990, p. 200). This positive slope generates a positive feedback effect, in which the preheated volumes have higher RF conductivity, therefore the RF current and energy deposition is higher in the preheated volumes which further raises the higher temperature of the focal volumes, which increases the conductivity even further.

In one preferred embodiment of the invention, for each pair of RF electrodes applied to the skin surface, at least one focused ultrasound source is applied between the electrodes. In another preferred embodiment, a single focal volume of the ultrasound source is created extending between the RF electrodes, to produce a guiding channel for the RF current.

Preferred frequencies of the RF energy are between 100 kHz and 100 MHz, and more preferred between 100 kHz and 10 MHz. Preferred ultrasound frequencies are between 500 kHz and 50 MHz, more preferred between 1 MHz to 20 MHz.

The apparatus of the invention preferably includes cooling means to lower the initial temperature of the treated area prior to the application of the energy sources. This leads to a larger temperature gradient between focal volumes to be heated and the remainder of the treated area. This allows heating of the focal volumes while avoiding excessively high temperatures in the tissues surrounding the focal volumes, which might damage the tissue there.

The RF and ultrasound energy are preferably applied for a short time duration, preferably as a pulse or a train of pulses (or several pulses), in order to reduce loss of heat from the focal volumes by conduction or convection. Application times for the ultrasound energy are preferably between 1 msec and 10 sec, more preferably between 10 msec and 1 sec. The RF energy preferably follows the ultrasound energy although some overlapping of the ultrasound and RF application is possible. The RF energy is preferably applied for times between 10 msec and 1 sec.

The temperature generated at the focal volumes by the energy sources and the time of heating are selected so that adequate heating of the focal volumes is obtained, while heating of surrounding tissues is minimal. The focal volumes are preferably heated to 50 to 90° C. At the lower end of this temperature range, tens of seconds may be needed to obtain a substantial effect and at the higher end of the range, subsecond heating may be sufficient. Damage to surrounding tissues might occur at temperatures close to and above 44° C. when the heating times are long, (e.g. tens of minutes). A temperature of 44° C. is also known as the threshold temperature for human pain perception. A more preferred time range, for the treatment is about few seconds or less, to prevent substantial heat flow from the focal volumes during the treatment. For that time range the preferred temperature range for effecting damage to the selected tissue is 60-70° C.

Thus, in its first aspect, the invention provides a system for treating skin comprising:
  one or more ultrasound transducers adapted to focus ultrasound energy at one or more focal volumes in the skin;
  one or more pairs of RF electrodes adapted to deliver RF energy to the one or more focal volumes.

In its second aspect, the invention provides method for treating skin comprising:
  heating the skin to a first temperature at one or more focal volumes in the skin by focusing ultrasound energy at the one or more focal volumes; and
  heating the one or more focal regions to a second temperature, the second temperature being higher than the first temperature, by generating an RF current in a region of the skin containing the one or more focal regions.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
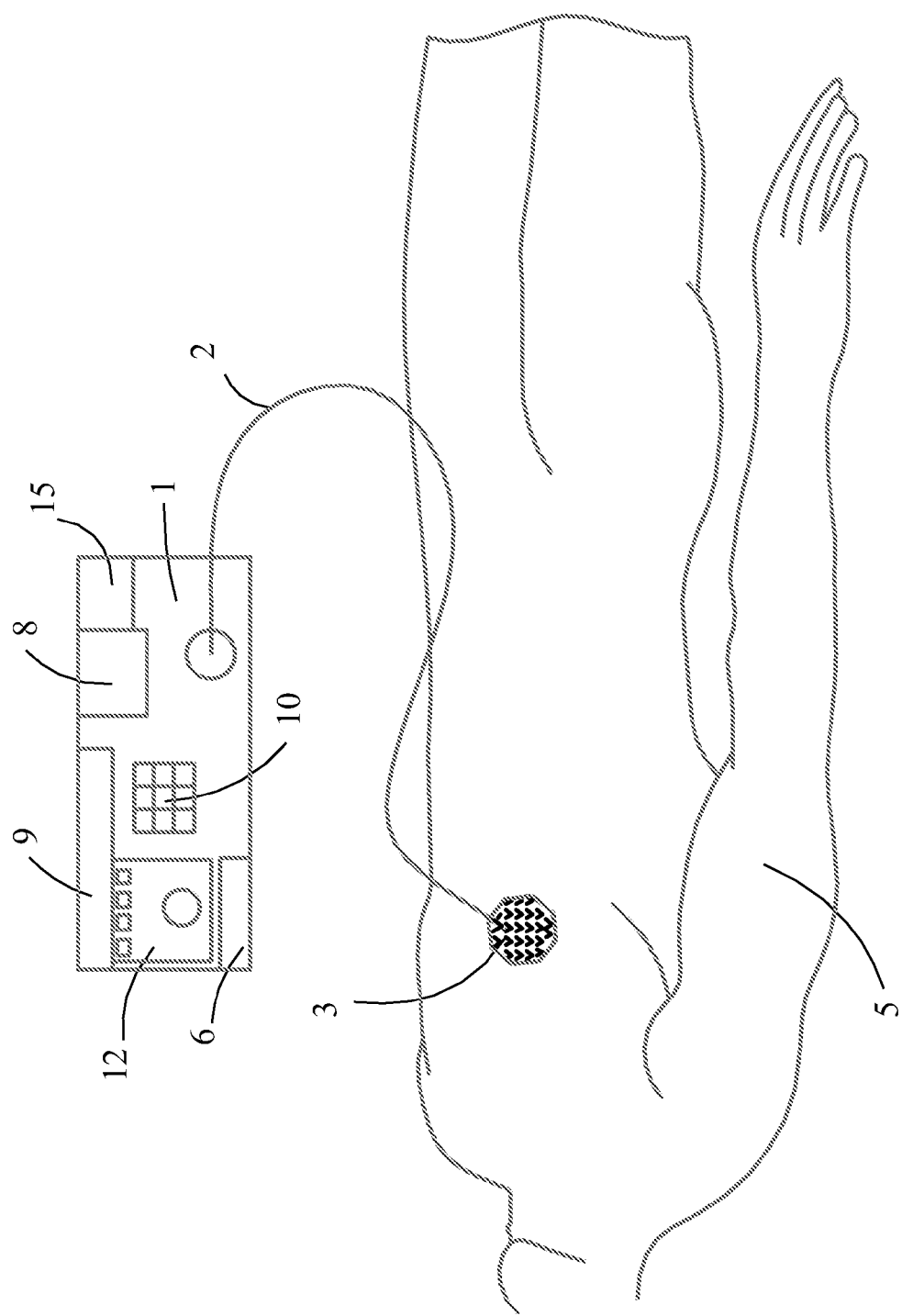
FIG. 1 shows a system for treating skin in accordance with one embodiment of the invention.

FIG. 1 shows a system for applying ultrasound and RF energies to skin tissue in accordance with one embodiment of the invention. An applicator 3, to be described in detail below, contains one or more pairs of RF electrodes and one or more ultrasound transducers. The applicator is adapted to be applied to the skin of an individual 5 in a region of skin to be treated. The applicator 3 is connected to a control unit 1 via a cable 2. The control unit 1 includes a power source 8. The power source 8 is connected to an RF generator 15 that is connected to the RF electrodes in the applicator 3 via wires in the cable 2. The power source 8 is also connected to an ultrasound driver 6. The driver 6 is connected to the transducers via wires in the cable 2. The control unit contains a refrigeration unit 12 that cools a fluid such as ethanol or water for cooling the applicator 3. The cooled fluid flows from the refrigeration unit 12 to the applicator via a first tube in the able 2, and flows from the applicator 3 back to the refrigeration unit via a second tube in the cable 2. The control unit 1 contains a processor 9 for monitoring and controlling various functions of the device. The control unit 1 has an input device such as a keypad 10 that allows an operator to input to the processor 9 selected values of parameters of the treatment, such as the frequency, pulse duration and intensity of the RF energy or the duration and intensity of the ultrasound energy or the depth of the focal volume below the skin surface. The processor may be configured to activate the ultrasound transducer for a first predetermined amount of time and then to apply an RF voltage to the RF electrodes for a second predetermined amount of time. The RF energy may be delivered to the skin surface before termination of the ultrasound energy, or the ultrasound energy may persist during the at least part of the time that the RF energy is applied. The processor 9 may also monitor the electrical impedance between the electrodes in the applicator 3, and determine the temperature distribution in the vicinity of the target. The processor may also determine the parameters of the treatment based upon the impedance measurements.

Figure 2:
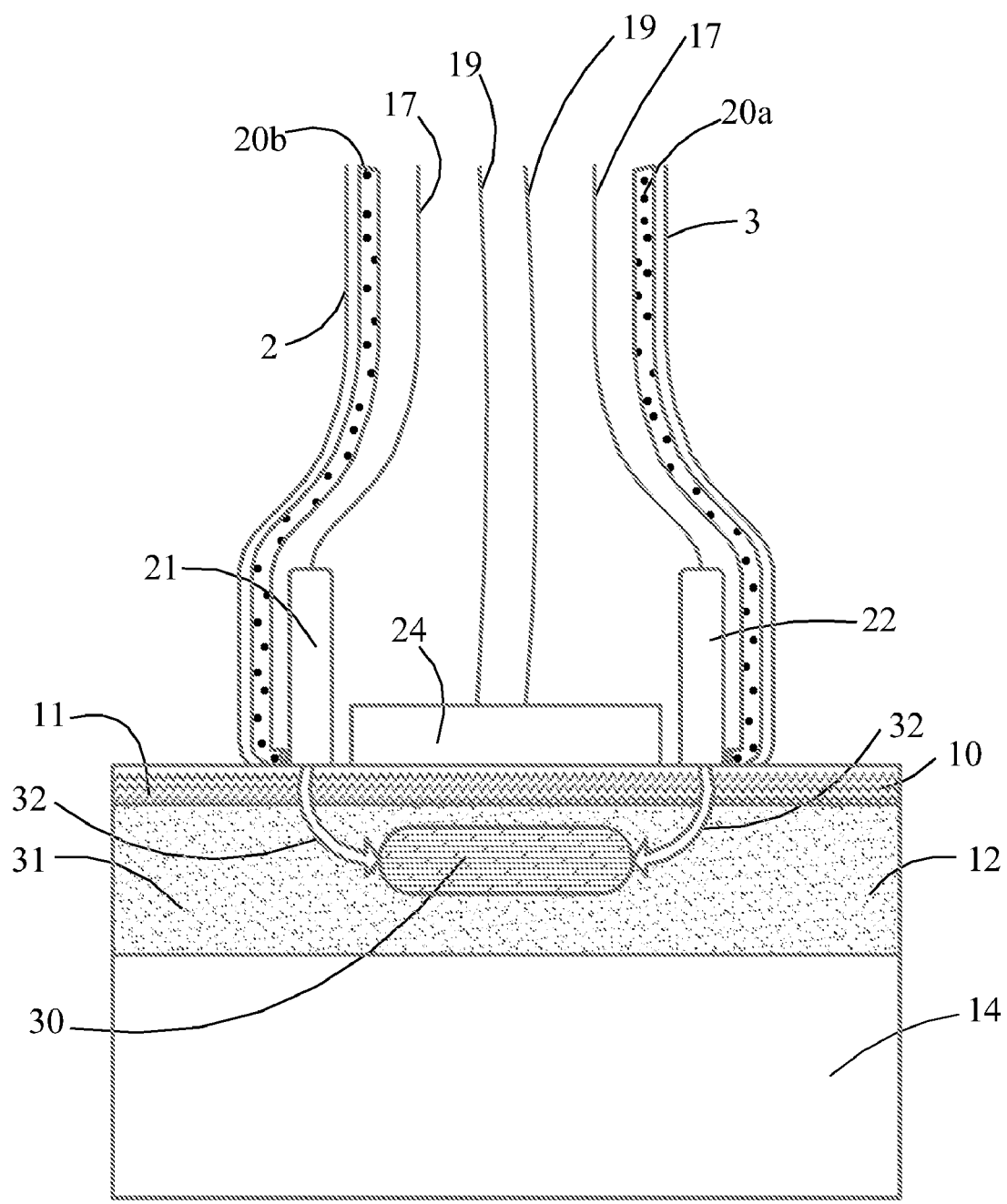
FIG. 2 shows an embodiment of an applicator for use in the system of FIG. 1.

FIG. 2 shows the applicator 3 in greater detail in accordance with one embodiment of the invention. The applicator is shown in FIG. 2 applied to a skin surface 11. Layer 10 is the epidermis, 12 is the dermis and 14 is the subcutaneous tissue. The applicator 3 includes a pair of RF electrodes 21 and 22 that are connected to the RF generator 15 via wires 17 in the cable 2. The applicator 3 also includes an ultrasound transducer 24 that is located in the applicator 3 and is connected to the driver 6 via wires 19 in the cable 2 so as to focus ultrasound radiation at one or more focal volumes 30 in the dermis 12. The applicator 3 contains a cooling coil that conducts a coolant from the refrigeration unit 12 via a first tube 20a in the cable 3 to the skin surface 11 and from the skin surface 11 back to the refrigeration unit 12 via a second tube 20b in the cable 3.

In accordance with the method of the invention, the applicator 3 is applied to the skin surface 11. Preferably, an ultrasound liquid gel is applied between the ultrasound transducer 24 and the skin surface 11 to facilitate acoustical matching and good energy transfer, and a conductive liquid or gel is applied between the RF electrodes 21 and 22 and the skin surface 11 to reduce contact resistance. Ultrasonic radiation from the transducer 24, is focused at the one or more focal volumes 30 located in the dermis layer 12. The ultrasound energy raises the temperature at the focal volumes above that of tissue volumes 31 surrounding the focal volumes. The normal dermal temperature is typically around 34° C., and with the ultrasound heating of the focal volumes 30, the temperature of the focal volumes rises. The slope of the electrical conductivity versus temperature is about 2-3° C. Thus, if the selected zone is heated by ultrasound to 10° C. above the normal dermal temperature, the electrical conductivity of the zone rises by 20-30%. An RF voltage is then applied from the RF generator 15 to the electrodes 21 and 22, so that an RF current 32 flows between electrodes 21, 22, through the tissue layers 10, 12, 14, with more current flowing through the pre-heated focal volume 30 due to its higher conductivity. The preferred spacing between the RF electrodes 21 and 22 is 0.2 cm to 2 cm, and more preferably, 0.5 cm to 1 cm. With a spacing of 1 cm between the electrodes, a typical voltage of 20 to 1000 Vrms, and more preferably 50 to 200 Vrms may be used. Lower voltages are required with smaller electrode spacings. For RF frequencies between 100 kHz and 100 MHz, the electromagnetic wavelength is much larger than the inter-electrode spacing. Also, the typical skin conductivity at these frequencies is about 0.5 S/m (see for example, S. Gabriel, R. W. Lau, and C. Gabriel, Phys. Med. Biol. 41 (1996), pp 2251-2269). For 10 MHz and 0.5 S/m the electromagnetic skin depth is 22 cm, much larger than the thickness of the human skin layer which is less than one centimeter. Under these conditions the current distribution is almost identical to the static solution obtained by Ohm's Law, $J=\sigma E$, where J is the current density and E is the electric field vector. The power delivered to a unit volume of tissue by the current is $J \cdot E = \sigma E^2$. The rate of increase of temperature increase is proportional to the power, and thus proportional to the conductivity, a positive feedback effect is generated since the conductivity increases with temperature.

Figure 3:
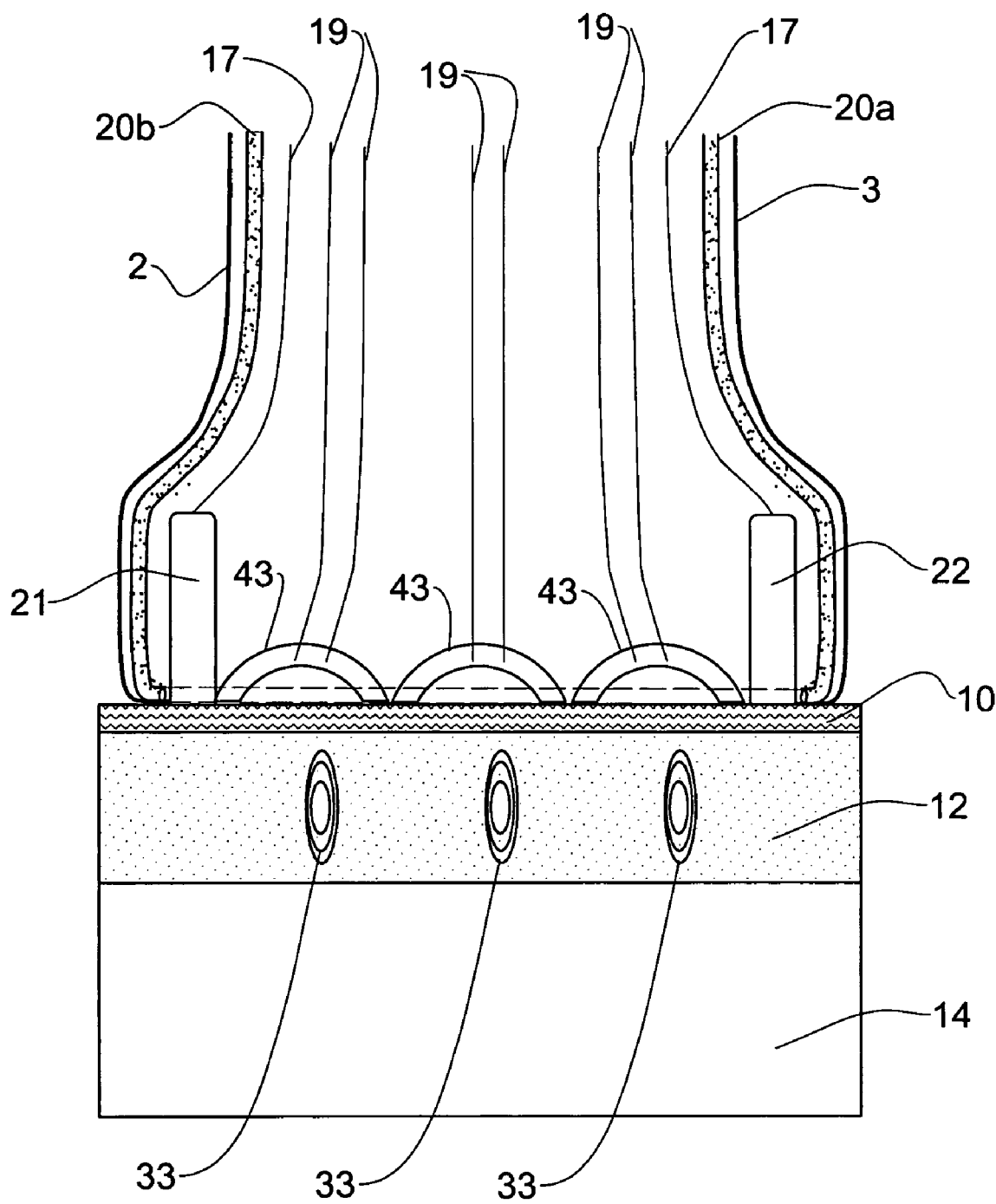
FIG. 3 shows another embodiment of an applicator for use in the system of FIG. 1.

The ultrasound transducer 24 may generate a single elongated focal zone 30, extending between the RF electrodes as shown in FIG. 2. FIG. 3 shows another embodiment of the applicator 3. The embodiment of FIG. 3 has elements in common with the embodiment of FIG. 2, and similar elements are indicated by the same reference numeral in FIGS. 2 and 3, without further comment. In the embodiment of FIG. 3, the applicator includes three ultrasound transducers 43 that generate three spaced about focal volumes 33. This is by way of example only, and the applicator may include any number of spaced apart ultrasound transducers 43, generating an equal number of focal volumes 33. The ultrasound transducers 43 have focal volumes 33 in the dermal layer 12. Heating of these focal volumes by the ultrasound energy heats the tissue to be treated which thus forms a guide channel for the RF energy, which further heats the tissue to the desired temperature. In this embodiment, a single pair of RF electrodes 21, 22 provides RF energy to all of the focal volumes 33. In another embodiment of the applicator 3 shown in FIG. 4, each ultrasound transducer 44 (44a, 44b, and 44c) is located between a respective pair of RF electrodes 28 (28a, 28b, and 28c), 29 (29a, 29b, and 29c). The plurality of ultrasound transducers can be driven altogether by a single power supply, or each one driven independently. This also applies to the RF electrodes. A single pair of electrodes driven by a single RF power supply, or a plurality of RF electrode pairs, each pair being driven independently. Each ultrasound transducer 44 and its respective RF electrodes should be matched in two respects: a. Space matching—the electric field generated by the RF electrode should cover the focal volume of the ultrasound transducer. b. Time matching between the application of the ultrasound energy and application of the RF energy, namely, starting with application of the ultrasound energy to the focal volumes and immediately follow with the application of RF energy to the skin.

The focal volume, in the direction normal to the skin surface, is preferably continued within the deeper layer of the epidermis, the dermis layer and part of the subcutaneous layer, so that the skin surface is not damaged, that is, between 0.2 mm and 5 mm deep, more preferably, between 0.2 mm to 2 mm. The lateral width of the focal zone may be 0.05 mm to 1 mm, more preferably from 0.1 mm to 0.3 mm. The lateral spacing between focal volumes is preferably between 0.3 mm to 3 mm, more preferably from 0.5 mm to 1 mm. In the longitudinal direction, which is that of the guiding channel between the RF electrodes, the length of the focal volumes may be 1 mm to 20 mm, more preferred 3 mm to 10 mm.

Figure 4:
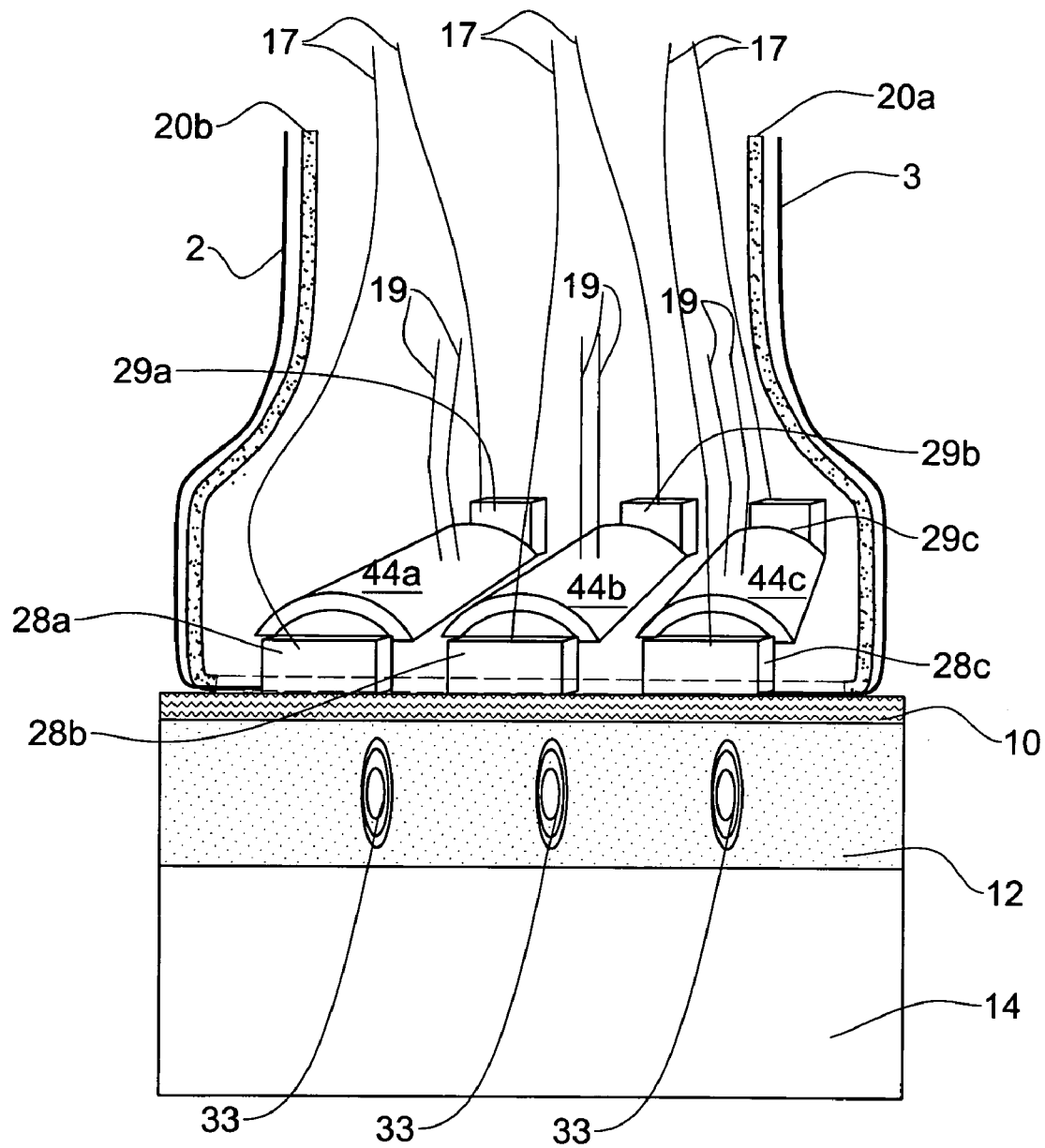
FIG. 4 shows a third embodiment of an applicator for use in the system of FIG. 1.

While FIG. 4 shows cylindrical ultrasound transducers having cylindrical focal volumes, other geometries are possible. An ellipsoidal focal zone may be generated with a hemispherical transducer or with flat a transducer and an acoustical lens. For this focal geometry, a plurality of RF electrodes can be applied, with a 1-dimensional or 2-dimensional structure of interlacing RF electrodes and ultrasound transducers.

The invention claimed is:

1. A system for generating a guided current path in a skin volume, said system comprising:
    (a) at least one transducer configured to focus ultrasound energy at least one focal volume in the skin and heat said volume so as to raise the volume electrical conductivity;
    (b) at least a pair of RF electrodes configured to deliver RF energy to the same focal volume; and
    (c) a control unit configured to enable an RF current generated by the RF energy to flow between the pair of RF electrodes through a central part of the heated focal volume,
    wherein the parameters of the RF energy are selected from the group consisting of a frequency of an RF voltage between 100 KHz and 100 MHz, an intensity of the RF voltage, and a duration of the RF energy, and
    wherein the ultrasound energy has a frequency between 500 KHz and 50 MHz.

2. The system according to claim 1, wherein the control unit is configured to:
    (a) activate at least one of the ultrasound transducer for a first predetermined amount of time; and
    (b) apply an RF voltage to the RF electrodes for a second predetermined amount of time.

3. The system according to claim 2, wherein said RF electrodes are configured to generate at least one of spatially matching or time matching with said skin volume affected by ultrasound electric field.

4. The system according to claim 3, wherein said space matching electric field generated by the RF electrodes covers the focal volume of the ultrasound transducer.

5. The system according to claim 3, wherein said time matching electric field generated by the RF electrodes is the time between the focusing of the ultrasound energy and delivery of the RF energy to the skin.

6. The system according to claim 1, wherein the at least one ultrasound transducer is configured to focus ultrasound energy to at least one focal volume located in a dermis layer of the skin.

7. The system according to claim 1, further comprising a cooling system cooling the skin surface.

8. The system according to claim 1, further comprising an applicator configured to be applied to the skin surface, the applicator containing the ultrasound transducer and the RF electrodes.

9. The system according to claim 8, wherein at least one pair of the RF electrodes and at least one of the ultrasound transducer are contained in the applicator in which the at least one ultrasound transducer is located between the pair of RF electrodes configured to generate electric current in the same ultrasound heated skin volume.

10. The system according to claim 1, wherein at least one of the focal volumes is located between 0.2 mm and 5 mm below the skin surface.

11. The system according to claim 10, wherein at least one of the focal volumes is located between 0.2 mm to 2 mm below the skin surface.

12. The system according to claim 1, wherein a lateral width of at least one of the focal volumes is between 0.05 mm to 1 mm.

13. The system according to claim 12, wherein the lateral width of at least one of the focal volumes is between 0.1 mm to 0.3 mm.

14. The system according to claim 1, wherein a lateral spacing between the focal volumes is between 0.3 mm to 3 mm.

15. The system according to claim 14, wherein the lateral spacing between focal volumes is between the 0.5 mm to 1 mm.

16. The system according to claim 1, wherein a longitudinal length of the focal volumes between the RF electrodes is between 1 mm to 20 mm.

17. The system according to claim 16, wherein the longitudinal length of the focal volumes between the RF electrodes is between 3 mm to 10 mm.

18. The system according to claim 1, wherein a electric field generated by the RF electrode coincides with the focal volume of the ultrasound transducer.

19. The system according to claim 1, wherein the delivery of the RF energy to at least one of the focal volumes of the skin immediately follows the focusing of the ultrasound energy to the same focal volumes.

20. A method for treating skin, said method comprising:
(a) heating at least one focal volume of the skin by focusing ultrasound energy at said focal volume to a first temperature, said temperature being sufficient to raise an electrical conductivity of said focal volume; and,
(b) increasing further the temperature of the same focal volume to a second temperature, the second temperature being higher than the first temperature, by guiding an RF current through said focal volumes with raised temperature;
wherein the RF current is generated by an RF energy frequency between 100 KHz and 100 MHz,
wherein the ultrasound energy has a frequency between 500 KHz and 50 MHz, and
wherein the RF current flows through a central part of the heated focal volume.

21. The method according to claim 20, wherein at least one of the focal volumes is located in a subcutaneous region of the skin.

22. The method according to claim 20, further comprising cooling the skin surface.

23. The method according to claim 20, wherein at least one of the focal volumes is located between 0.2 mm and 5 mm below the skin surface.

24. The method according to claim 23, wherein at least one of the focal volumes is located between 0.2 mm to 2 mm below the skin surface.

25. The method according to claim 20, wherein a lateral width of at least one of the focal volumes is between 0.05 mm to 1 mm.

26. The method according to claim 25, wherein the lateral width of one or more of the focal volumes is between 0.1 mm to 0.3 mm.

27. The method according to claim 20, wherein a lateral spacing between focal volumes is between 0.3 mm to 3 mm.

28. The method according to claim 27, wherein the lateral spacing between focal volumes is between 0.5 mm to 1 mm.

29. The method according to claim 20, wherein a length of the focal volumes between the RF electrodes is between 1 mm to 20 mm.

30. The method according to claim 29, wherein the length of the focal volumes between the RF electrodes is between 3 mm to 10 mm.

31. A system for skin treatment, said system comprising:
(a) at least one ultrasound transducer configured to focus ultrasound energy into at least one focal volume in the skin operative to raise the electrical conductivity of said volume and generate at least one guided RF current path;
(b) at least one pair of RF electrodes configured to deliver RF energy to pass along a longitudinal direction into the same volumes forming said guided RF current paths; and
(c) a control unit configured to enable an RF current generated by the RF energy to flow between the pair of RF electrodes through a central part of the focal volume,
wherein the RF energy has a frequency between 100 KHz and 100 MHz, and
wherein the ultrasound energy has a frequency between 500 KHz and 50 MHz.

32. A method for treating skin, said method comprising:
(a) heating the skin to a first temperature at one or more focal volumes in the skin by focusing ultrasound energy at the one or more focal volumes;
(b) heating the one or more focal volumes to a second temperature, the second temperature being higher than the first temperature, by generating an RF current passing along the longitudinal direction of the same focal volumes; and
(c) controlling the RF current to flow through a central part of the heated focal volume,
wherein the RF current is generated by an RF energy frequency between 100 KHz and 100 MHz, and
wherein the ultrasound energy has a frequency between 500 KHz and 50 MHz.

33. A method for generating a guided current path in the skin, said method comprising:
(a) applying to the skin surface at least one ultrasound energy focused into the skin and operating to heat a focal volume to a first temperature sufficient to raise the temperature of said focal volume;
(b) increasing the temperature of the same focal volume by applying to said skin surface RF energy and guiding an induced RF current into the same focal volumes with raised temperature by the ultrasound energy; and (c) controlling the RF current to flow through a central part of the heated focal volume, wherein the RF energy frequency is between 100 KHz and 100 MHz, and wherein the ultrasound energy has a frequency between 500 KHz and 50 MHz.

34. A method for skin treatment, said method comprising:
a) applying to the skin to be treated a system including:
(i) at least one ultrasound transducer adapted to focus ultrasound energy at one or more focal volumes in the skin and heat said volumes such that their electrical conductivity is increased in said at one or more focal volumes in the skin; and
(ii) at least one pair of RF electrodes adapted to deliver RF energy to the same focal volume;
b) generating at least one guided RF current path in said volume; and
c) conducting RF induced current through the guided RF current path;
wherein the RF current flows through a central part of the heated focal volume,
wherein the RF energy frequency is between 100 KHz and 100 MHz, and
wherein the ultrasound energy frequency is between 500 KHz and 50 MHz.

35. A system for skin treatment, said system comprising:
a) at least one pair of RF electrodes configured to induce RF current in a guiding channel produced in the skin; and
b) at least one focused ultrasound source applied between the RF electrodes,
wherein the ultrasound source, by heating the skin to a temperature higher than the surrounding skin, creates in the skin a single guiding channel for the RF current, said channel extending between the RF electrodes,
wherein the RF current is generated by an RF energy frequency between 100 KHz and 100 MHz, and
wherein the ultrasound source generates an ultrasound energy frequency between 500 KHz and 50 MHz,
said system further comprising:
c) a control unit configured to enable the RF current to flow between the pair of RF electrodes through a central part of the single guiding channel.

36. A system for skin treatment, said system comprising:
a) at least one ultrasound transducer configured to generate a single elongated focal zone in a volume of the skin and raise the temperature of the focal zone to a first temperature higher than the temperature of the surrounding skin; and
b) a single pair of RF electrodes extending along the elongated focal zone and driven by a single RF power supply, said RF electrodes being configured to be applied to the skin and generate, in the elongated focal zone, a time and spatially matching the ultrasound generated elongated focal zone electric field and heat the same elongated focal zone to a second temperature higher than the first temperature,
wherein application of the ultrasound energy heats the elongated focal zone and generates a guided channel further heated by RF energy applied to the elongated focal zone,
wherein the RF energy has a frequency between 100 KHz and 100 MHz, and
wherein the ultrasound energy has a frequency between 500 KHz and 50 MHz,
said system further comprising:
c) a control unit configured to enable an RF current generated by the RF energy to flow between the pair of RF electrodes through a central part of the elongated focal zone.

37. A system for skin treatment, said system comprising:
a) one or more cylindrical ultrasound transducers configured to produce in the skin one or more cylindrical focal volumes with each transducer heating a respective focal volume;
b) a plurality of RF electrodes with a 1-dimensional or 2-dimensional structure interlacing with the ultrasound transducers and configured to be applied to the skin to heat further the same cylindrical focal volumes heated by the ultrasound transducer; and
c) a control unit configured to enable an RF current generated by an RF energy to flow between the plurality of RF electrodes through a central part of the heated cylindrical focal volume,
wherein the RF electrodes produce the RF energy having a frequency between 100 KHz and 100 MHz, and
wherein the ultrasound transducer produces an ultrasound energy having a frequency between 500 KHz and 50 MHz.

* * * * *